(12) United States Patent
Rueggeberg

(10) Patent No.: US 7,938,643 B2
(45) Date of Patent: May 10, 2011

(54) USE OF INTEGRATING SPHERE TECHNOLOGY TO PROVIDE UNIFORM, HIGH-INTENSITY LIGHT, AND WAVELENGTH MIXING FROM LIGHT EMITTING DIODES

(75) Inventor: Frederick A. Rueggeberg, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 32 days.

(21) Appl. No.: 12/018,480

(22) Filed: Jan. 23, 2008

(65) Prior Publication Data

US 2008/0131836 A1 Jun. 5, 2008

Related U.S. Application Data

(63) Continuation-in-part of application No. 11/620,256, filed on Jan. 5, 2007.

(60) Provisional application No. 60/756,862, filed on Jan. 7, 2006.

(51) Int. Cl.
*A61C 1/00* (2006.01)
*A61C 15/00* (2006.01)

(52) U.S. Cl. .......................... 433/29; 433/215

(58) Field of Classification Search .......... 433/29, 433/215–229; 356/236
See application file for complete search history.

(56) References Cited

U.S. PATENT DOCUMENTS

| | | | | |
|---|---|---|---|---|
| 1,979,952 A | * | 11/1934 | Benford | 356/448 |
| 4,232,971 A | * | 11/1980 | Suga | 356/446 |
| 4,873,430 A | * | 10/1989 | Juliana et al. | 250/225 |
| 5,258,363 A | * | 11/1993 | Hed | 505/160 |
| 5,745,234 A | * | 4/1998 | Snail et al. | 356/236 |
| 5,823,950 A | | 10/1998 | Diab et al. | |
| 6,102,696 A | * | 8/2000 | Osterwalder et al. | 433/29 |
| 6,208,788 B1 | * | 3/2001 | Nosov | 385/121 |
| 6,331,111 B1 | * | 12/2001 | Cao | 433/29 |
| 6,422,718 B1 | * | 7/2002 | Anderson et al. | 362/296.03 |
| 7,508,503 B2 | * | 3/2009 | Jang | 356/236 |
| 2002/0182563 A1 | * | 12/2002 | Boutoussov et al. | 433/29 |

(Continued)

FOREIGN PATENT DOCUMENTS

JP 7212537 8/1995

OTHER PUBLICATIONS

Allen, S.C., Heikenfeld, J., Stecki, A.J.; Hybrid Inorganic/Organic Devices for Solid State White Lighting Applications; date unknown; 3 pages; University of Cincinnati, Nanoelectronics Laboratory, Department of Electrical Engineering, and Extreme Photonix, LLC, Cincinnati, Ohio, USA.

(Continued)

*Primary Examiner* — Cris L Rodriguez
*Assistant Examiner* — Yogesh Patel
(74) *Attorney, Agent, or Firm* — Thomas, Kayden, Horstemeyer & Risley, LLP

(57) ABSTRACT

An illumination device including an integrating sphere and at least one light source. The integrating sphere is hollow and houses the at least one light source in it. The light source can be manipulated between a first configuration and a second configuration. The illumination device emits a first spectrum of light when the light source is in the first configuration, and a second spectrum of light when the light source is in the second configuration.

10 Claims, 3 Drawing Sheets

U.S. PATENT DOCUMENTS

| | | | |
|---|---|---|---|
| 2003/0215766 A1 | 11/2003 | Fischer et al. | |
| 2005/0003323 A1* | 1/2005 | Katsuda et al. | 433/29 |
| 2006/0166161 A1* | 7/2006 | Rose et al. | 433/29 |
| 2007/0020578 A1 | 1/2007 | Scott et al. | |
| 2007/0246732 A1 | 10/2007 | Sakuma et al. | |

OTHER PUBLICATIONS

Brown, Steven W., Santana, Carlos, Eppeldauer, George P.; Development of a Tunable LED-Based Colorimetric Source; J. Res. Natl. Inst. Stand. Technol.; 2002; pp. 363-371; vol. 107; Gaithersburg, MD.

* cited by examiner

USE OF INTEGRATING SPHERE TECHNOLOGY TO PROVIDE UNIFORM, HIGH-INTENSITY LIGHT, AND WAVELENGTH MIXING FROM LIGHT EMITTING DIODES

CROSS-REFERENCE TO RELATED APPLICATION

This application is a continuation-in-part of U.S. Non-Provisional patent application Ser. No. 11/620,256, filed Jan. 5, 2007, which claims the benefit of U.S. Provisional Patent Application Ser. No. 60/756,862, filed Jan. 7, 2006. Said applications are incorporated herein by reference in their entireties for all purposes.

TECHNICAL FIELD

The present invention relates generally to the field of lighting and illumination equipment, and more particularly, to lighting equipment that utilizes integrating sphere technology.

BACKGROUND OF THE INVENTION

Generally, a single light fixture having a light source emits a predetermined range of light wavelengths when in operation. Typically, the light wavelength range cannot be changed without alternating the light source for another that emits a different range of light wavelengths or with the use of specific filters that allow passage of only a selected bandwidth. However, there are numerous circumstances that require the use of different wavelengths of light. Presently, to meet these needs, a user is required to use multiple light fixtures or alternate various light sources within a single fixture, for example by changing the light fixture's bulb, or by filtering the light emitted from the fixture to permit only the passage of certain light wavelengths.

In the field of dentistry, for example, illumination of the oral cavity during the performance of chair-side dental work currently focuses on merely providing sufficient lighting to illuminate the oral cavity. Typically, the necessary illumination is provided by quartz-tungsten-halogen operatory lights that emit a broad pattern of irradiation. However, most restorative materials used in dentistry are polymerized by exposure to visible light. Specifically, restorative materials are most sensitive to the wavelengths associated with the perception of the color blue (425-490 nm). In fact, many restorative products are very sensitive to light, such that it is not atypical for irradiance from the operatory lights to initiate polymerization of the restorative material as it is being applied by the dentist, which can result in pre-mature curing. Presently, to alleviate this problem, a blue-light filter is placed between the light source and a patient's mouth to remove the wavelengths of light that cause pre-mature polymerization. For instance, a dentist's assistant often holds a "blue-blocker" plastic paddle in-between the light source and the patient's mouth to filter out the necessary wavelengths of light. However, this process often restricts the assistant from assisting the dentist in other ways during this time.

Also, when performing tooth restorations, dentists have a difficult time correctly matching the color shade of a restored tooth to the surrounding teeth. In fact, tooth restorations are perceived to be different colors when exposed to different wavelengths of light. For example, tooth restorations look different when exposed to fluorescent lighting, incandescent lighting, or natural light from the sun. A dentist is therefore required to expose the restoration to multiple light sources in order to determine an all-around color shade that best matches the surrounding teeth.

In other medical fields, phototherapy and photodynamic therapy are rapidly becoming routine treatment options for many ailments. Often infrared light emitting diodes (LED's) are used as warming devices to stimulate blood circulation and/or to initiate tissue repair. Other skin diseases, such as psoriasis and vitiligo, are treated with specific wavelengths of light, although the particular wavelengths of light are often very different for each disease. The field of photodynamic therapy relies on the application of controlled wavelengths of light to body surfaces. Application of this light will then "activate" a medication that has been injected or ingested by the patient at the specific site of irradiation. Therefore, to initiate medical treatment, a variety of light fixtures are required depending on the particular ailment.

Other industries also have needs for applying various wavelengths of light: either simultaneously, or independently. For instance, theaters often utilize numerous light fixtures that each generate a specific color and wavelength range of light. The color industry also utilizes many different types of light fixtures to test different lighting conditions on certain types of paint, wallpaper, or other products. The illumination of vehicles (cars, trucks, boats, etc.) are based on an existing standard of position and color output to designate a purpose: headlights, directional signals, turn signals, starboard, port, etc. In each instance, a different illuminant source and/or filters are required for each color needed. Therefore, the problem common to all of these industries, and others, is that different light fixtures or filters are required to generate a variable range of light wavelengths.

Therefore, it can be seen that a need exists for a single light fixture that is capable of generating variable spectrums of light. It is to the provision of this need and others that the present invention is primarily directed.

SUMMARY OF THE INVENTION

The present invention provides a lighting apparatus that is capable of emitting a user-determined range of light wavelengths. The range of light wavelengths is variable by the user so that the user can manipulate the lighting apparatus as desired for a particular application. An advantage of the present invention over known light fixtures is that, because of its ability to emit the wavelength of light desired by the user, the present invention is capable of replacing a multitude of traditional light fixtures, which themselves typically only emit a set range of light wavelengths.

In one aspect, the present invention is an illumination device including an integrating sphere and at least one light source. The integrating sphere is hollow, coated with a reflective film, and houses the at least one light source within it. The light source can be manipulated between a first configuration and a second configuration. The illumination device emits a first spectrum of light when the light source is in the first configuration, and a second spectrum of light when the light source is in the second configuration.

In another aspect, the invention is a dental light fixture for use with teeth restoration. The fixture includes an integrating sphere having an exit aperture, at least one light source housed within the integrating sphere for emitting light, and a collimating, dispersive, or focusing lens coupled to the exit aperture for collecting and directing the light emitted by the at least one light source. The fixture emits a first spectrum of light when in a first configuration and a second spectrum of light when in a second configuration.

In another aspect, the invention is a method of restoring a tooth using dental restoration materials. The method includes the following steps: applying restoration materials to the tooth while illuminating the tooth with light emitted from a dental light fixture in a first configuration, and illuminating the tooth with light emitted from the dental light fixture in a second configuration once the materials have been applied to the tooth. The light emitted from the fixture in the first configuration does not contain a spectrum of light having a substantial physical effect upon the restoration materials, and the light emitted from the fixture in the second configuration contains a spectrum of light having a substantial physical effect upon the restoration materials.

In still another aspect, the invention is an illumination device including an internally reflective enclosure, a first light source, a second light source, and at least one switch for selectively illuminating the first and second light sources. The first light source emits light of a first wavelength within the internally reflective enclosure and the second light emits light of a second wavelength within the internally reflective enclosure.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
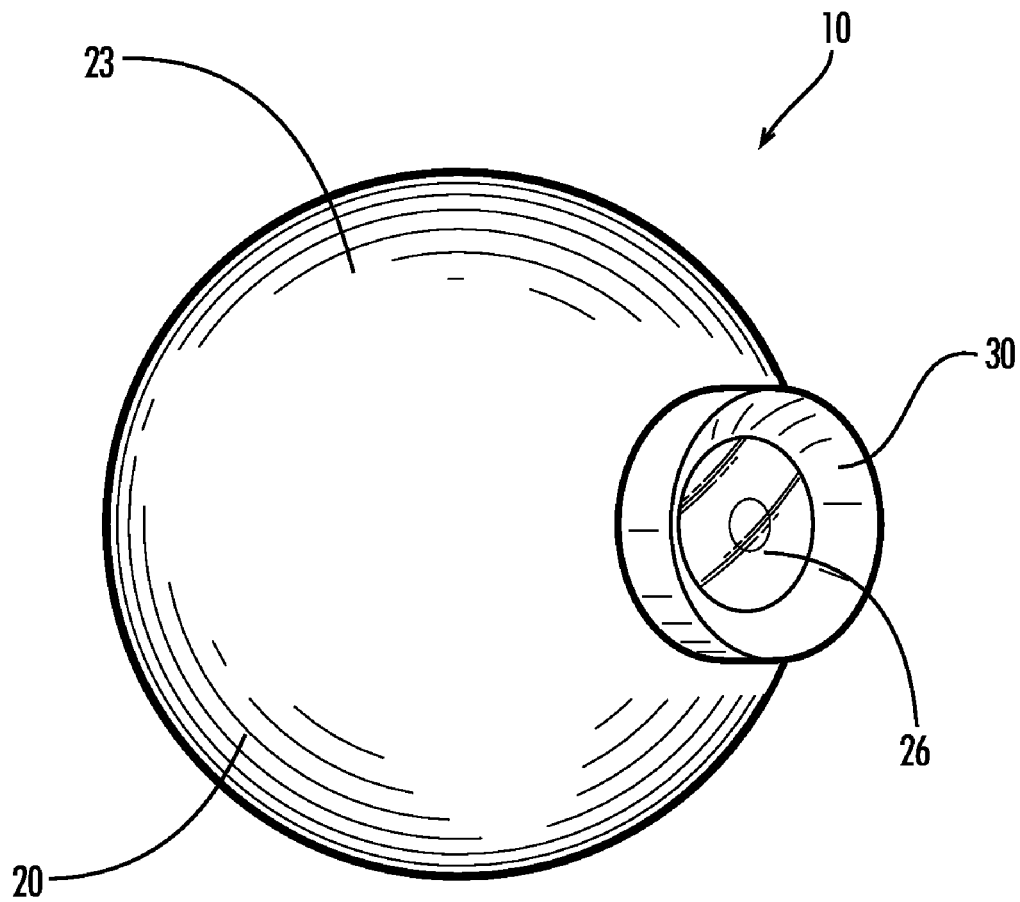
FIG. 1 is a perspective view of an integrating light fixture according to a first example embodiment of the present invention.
Figure 2:
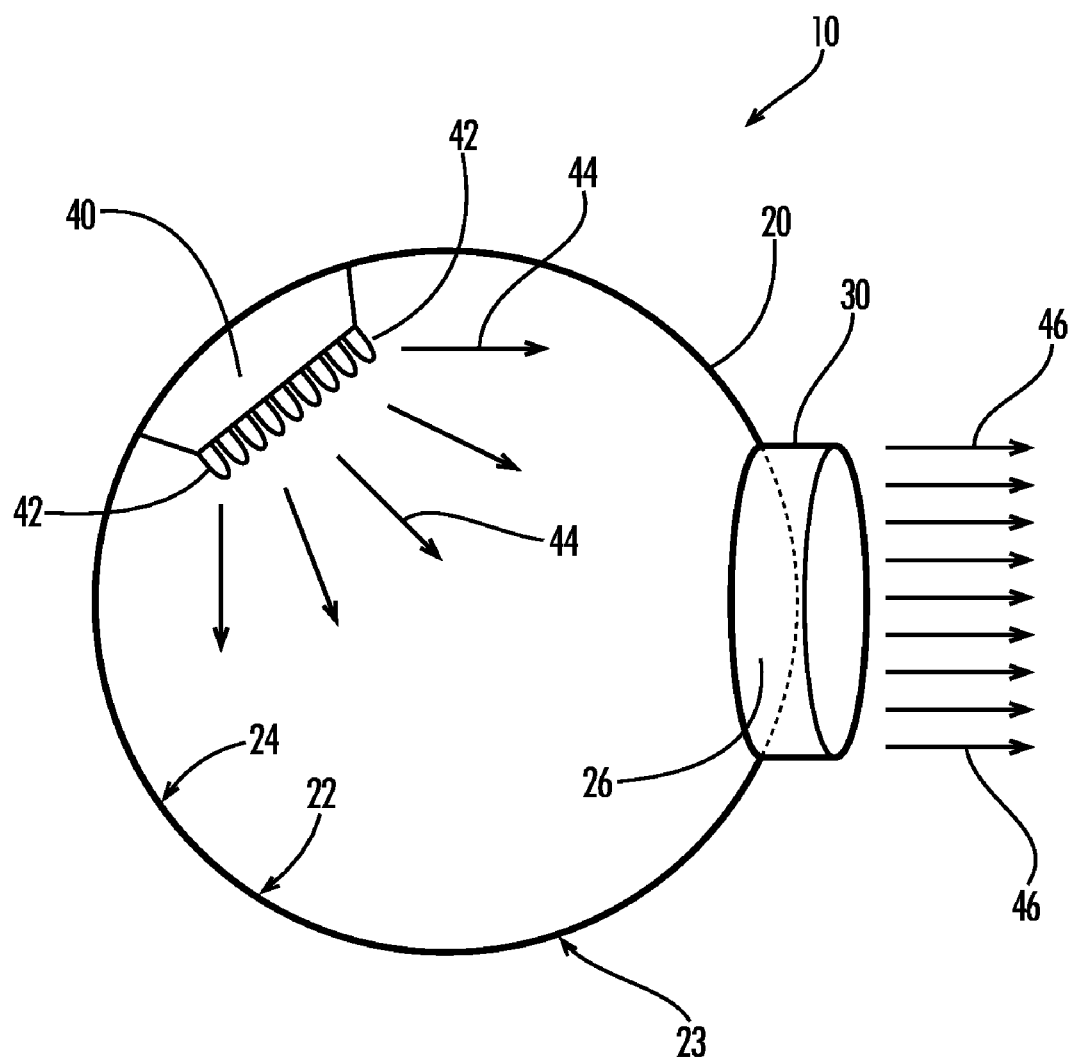
FIG. 2 is a perspective view of the integrating light fixture of FIG. 1, showing the interior of the fixture for clarity.

With reference now to the drawing figures, FIGS. 1-2 depict an integrating light fixture 10 according to a first example embodiment of the present invention. The light fixture 10 generally comprises an integrating sphere 20, a collimating, dispersive, or focusing lens 30, and at least one light source 40. The light source 40 may consist of a number of individual light sources of differing wavelength emissions. The light fixture 10 is capable of emitting a user-determined range of light wavelengths that is variable. As such, the light fixture 10 can be used in place of a multitude of traditional light fixtures, which typically emit a set range of light wavelengths. As mentioned previously, the present invention can be of particular use to the medical field, including dentist restoration work and phototherapy, along with other applications that will be discussed in greater detail below.

Integrating spheres, such as the one used in the present invention, are typically used to measure the total light output of a light source. For example, the light source being tested is placed in the center of the sphere and a light meter is located on one side. The inside of the sphere is typically coated in a highly reflective material to permit a tremendously high percentage of the light emitted from the source to reflect off of the sphere's internal surface. The light from the light source reflects around the interior of the sphere until it reaches the light meter, where the output of the lamp is measured and quantified. Because the light is neither absorbed by the internal coating nor permitted to escape the sphere, and is uniformly scattered and mixed to homogeneity in intensity, integrating spheres are extremely accurate measurement tools for determining the output of a light source. The present invention takes advantage of these properties and utilizes the integrating sphere for a different purpose: to create a light fixture capable of outputting variable spectrums of light, and also homogeneously mixing them.

The integrating sphere 20 of the present invention, as depicted in FIG. 2, includes an interior surface 22 and exterior surface 23, wherein the interior surface is covered in a highly reflective coating 24 such as gold, nickel, cadmium, aluminum, silver, alumina, Spectralon®, and/or other commercially available products. The integrating sphere 20 can range tremendously in size and diameter D1 depending on the application and needs of a user. For example, the sphere 20 can range from 2.5 cm to 2 meters. The integrating sphere 20 also includes an exit aperture 26, which forms a hole in the exterior of the sphere. The exit aperture 26 allows the light from the interior of the sphere 20 to exit. The diameter D2 of the exit aperture 26 can also vary widely depending on the needs of the user. If a smaller beam is desired by the user, a smaller diameter exit aperture can be utilized, such that in example embodiments D2 is about ¼ to ½ the length of D1. Conversely, if a larger light beam is desired, a larger diameter exit aperture may be used, such that in other embodiments D2 is about ½ to ¾ the diameter of D1. In alternative embodiments, a single adjustable exit aperture 26 is utilized to manipulate the diameter D2 of the exit aperture to meet the user's specific needs with respect to spot size on the target and intensity.

The light fixture 10 also includes at least one light source 40. The light source 40 can comprise any type of bulb such as an incandescent, fluorescent, or LED bulb, an array, or a combination thereof. However, in preferred embodiments, the light source 40 comprises a plurality of LED's 42 as shown in FIG. 2. When the LED's 42 are in operation, light 44 emitted from the LED's reflects along the coated interior surface 22 of the integrating sphere 20 until it reaches the exit aperture 26. Because of the highly reflective surface 24 of the sphere 20, a high proportion of the light 44 emitted from the LED's 42 reaches the exit aperture 26. In example embodiments, each LED 42, or groups of LED's, can be independently operated and each individual LED, or groups of LED's, can emit a particular wavelength of light, such that a user can turn on/off a particular range of light wavelengths as desired. Additionally, it is preferred that the intensity of each LED, or group of LED's, be controlled. In such embodiments, the light source 40 can be manipulated into multiple configurations to allow a user to precisely vary the spectrum of light output. Therefore a user can utilize the light fixture 10 to emit many different spectrums of light without the aid of filters and without having to change out the light source. For example, a particular group of LED's can emit light in the red-light spectrum, while a second group of LED's can emit light in the blue-light spectrum, while a third group of LED's can emit light in the yellow-light spectrum. Then, a user can control the color of the light that is emitted by the fixture 10 by simply regulating how much of each color is emitted within the integrating sphere 20. In other example embodiments, the user can manipulate the fixture 10 into different configurations, wherein each configuration emits a different spectrum of light, with a remote control or by utilizing controls built into the fixture, such as one or more buttons or switches. In still other example embodiments, the switches or buttons can activate specific predetermined spectrums of light (e.g. blue light) as desired by the user.

Because of the sphere's 20 shape, each light beam 44 emitted from the light source 40 is traveling in a different direction as it reaches the exit aperture 26. Therefore, in example embodiments, a lens shaping system (collimating, focusing, dispersing lens) 30 is coupled to the open end of the integrating sphere 20 and located over the exit aperture 26. The collimating, focusing, or dispersing lens 30 gathers all of the light 44, regardless of the direction that the light is traveling as it reaches the lens, and directs the light into one parallel beam 46. By directing the light into a shaped beam (collimated, focused, or diffused), the lens 30 permits a user to focus the light towards a particular area or application. Without the collimating lens 30, the light from the light source 40 would quickly diverge and diffuse as it left the exit aperture 26. In other example embodiments, light may be directed to dispersive or focusing elements, optical fibers or mirrors are used to transport the light from the lens 30 or exit aperture 26 to the application site as needed by the user.

Figure 3:
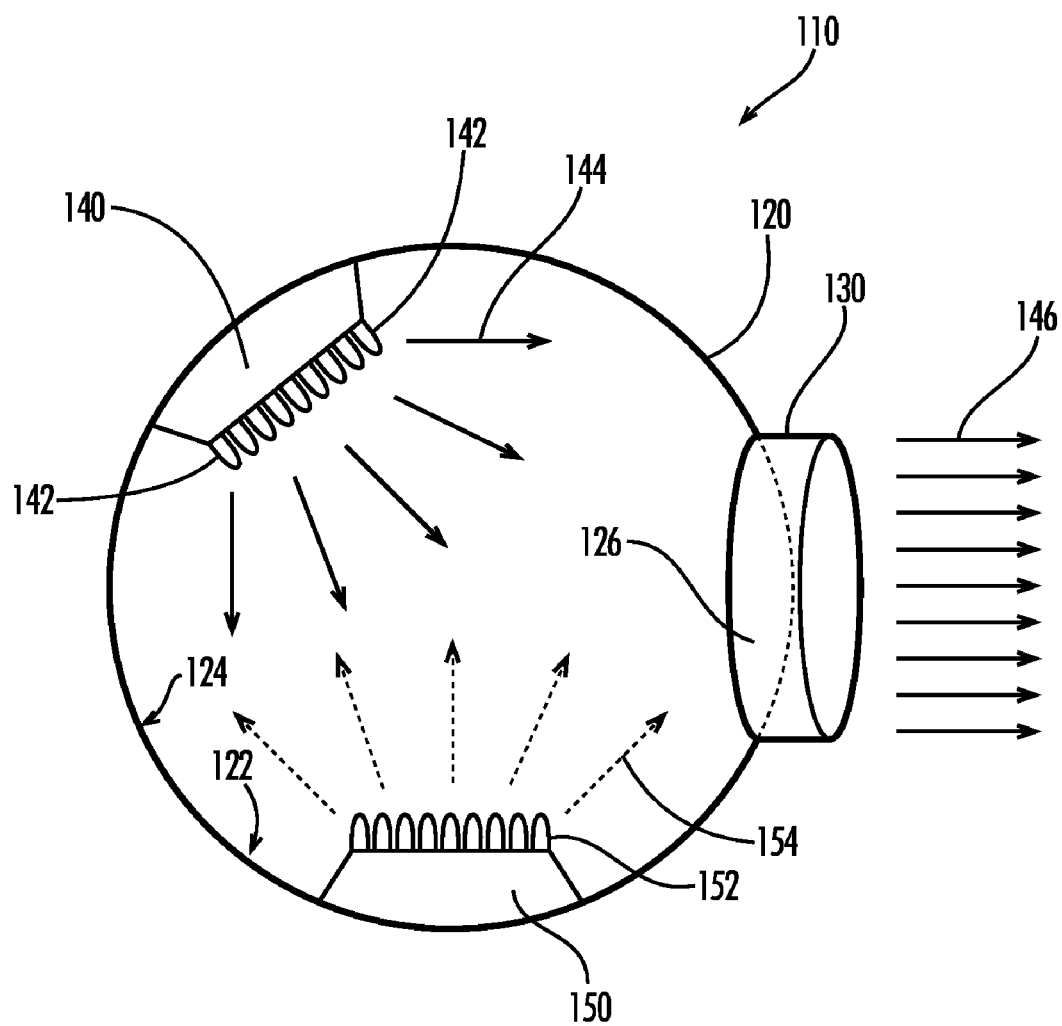
FIG. 3 is a perspective view of an integrating light fixture according to a second example embodiment of the present invention, showing the interior of the fixture for clarity.

A second example embodiment of an integrating light fixture 110 according to the present invention is depicted in FIG. 3. Similar to the first embodiment, the light fixture 110 comprises an integrating sphere 120, a collimating, focusing, or dispersing lens 130, a first light source 140, and a second light source 150. In alternative embodiments, additional sources of light are used in conjunction with the present invention, such as three, four, five or more independent light sources. It is preferred, but not necessary, that each light source is comprised of LED's (142,152). The light fixture 110 is extremely well suited for the field of restoration dentistry, although it can be equally useful in many other medical and non-medical applications.

As seen in FIG. 3, the significant difference between the first and second embodiments is the use of multiple light sources. In example embodiments, the first and second light sources 140,150 each emit separate ranges of light wavelengths. The light sources 140,150 can comprise a plurality of LED's 142,152, or other types of bulbs can be used (e.g. incandescent bulbs or fluorescent bulbs). Regardless of the types of bulbs used, the user can independently operate each light source, such that a user can utilize the light fixture 110 with both light sources on, one light source on/other light source off, or both light sources off. In the field of restoration dentistry, for example, when a dentist is working with restorative materials the dentist must currently not expose the materials to blue light (especially 425-490 nm) in order to prevent the materials from prematurely curing. Therefore, the first light source 140 can emit light wavelengths 144 covering the visible light spectrum (380-780 nm) excluding blue light, while the second light source 150 can emit light wavelengths 154 covering only blue light—or vice versa. Although dentist restoration materials are currently most sensitive to blue light, other embodiments of the present invention can emit light spectrums variable between any wavelength of light in which restoration materials are sensitive (e.g. red light, yellow light, infrared light, visible light, and/or ultraviolet light). In addition, a combination of wavelengths can be provided such that only those causing a given reaction are excluded, thus still providing illumination to the target, but without including undesired wavelengths.

In operation, a dentist performing restoration work, can utilize the light fixture 110 with both light sources 140,150 on to maximize light output, while providing a wide spectrum of light until the restorative materials are to be exposed. When both of the light sources are on, light 144 emitted from light source 140 and light 154 emitted from light source 150 reflect along the interior surface 122 of the sphere 120. Again, because the interior surface 122 of the sphere is coated with a highly reflective material 124, the light 144,154 reflects and mixes homogeneously until it exits the exit aperture 126. Once the light exits the aperture 126 it is received by the collimating, focusing, or diffusing lens 130. Similar to the first embodiment, the collimating, focusing, or dispersing lens 130 creates a shaped light beam 146 that can be directed as desired by the user. The light beam 146 comprises light from both light sources 140,150. When the dentist must expose the restorative materials, the second light source 150 can be turned off, such that only light from the first light source 140 is emitted from the fixture 110. Therefore, the light fixture 110 no longer emits wavelengths of light that cause premature curing of the restoration materials, but still emits a significant portion of the visible spectrum to allow the dentist a sufficient amount of light to perform his work without the need for light filters. When the dentist is ready for the restorative materials to begin curing, the dentist can again turn on the second light source 150 such that blue-light, or other spectrums of light that cause the restoration materials to cure, is emitted. When curing the restorative materials, the dentist can leave the first light source 140 on, or it can be turned off. To switch between the operation of the first light source and/or the second light source, a switch or button can be utilized to activate/inactivate the light sources.

In other example embodiments of the present invention, the light fixture 110 can be used for theatrical lighting. In such embodiments, the integrating sphere 120 can enclose several light sources representing the many colors that comprise white-light. By manipulating the intensity and amount of each color that is projected from the light sources within the fixture 110, the user can change the color of light that is emitted from the fixture.

In still other example embodiments, similar features can be employed for use with applications such as window lighting displays, color matching and shading, phototherapy, photodynamic therapy, other medical applications, as well as in the automotive, airplane, and boating industries.

While the invention has been described with reference to preferred and example embodiments, it will be understood by those skilled in the art that a variety of modifications, additions and deletions are within the scope of the invention, as defined by the following claims.

What is claimed is:

1. A method for projecting light into an oral cavity comprising:
   providing an overhead dental operatory light comprising an integrating sphere that includes an inner reflective surface and an exit aperture, a light source configured to emit light within the integrating sphere, and a lens provided at the exit aperture of the integrating sphere, the light source comprising a plurality of individual light elements, the light elements being configured to emit light at different wavelengths;
   activating the light source to emit light through the exit aperture into the oral cavity; and
   selectively controlling the intensity of the individual light elements to change the spectrum of light emitted by the light fixture so that the oral cavity can be viewed under visible fight that specifically excludes blue wavelengths that can inadvertently initiate curing of certain materials.

2. The method of claim 1, wherein the lens of the overhead dental operatory light comprises a collimating, focusing, or diffusive lens.

3. The method of claim 1, wherein the individual light elements comprise light emitting diodes.

4. The method of claim 1, wherein the light elements are arranged in groups of light elements, each group being configured to emit a different spectrum of light.

5. The method of claim 1, wherein the integrating sphere defines a spherical interior space and the light source is positioned within the spherical interior space.

6. The method of claim 1, wherein the inner reflective surface of the integrating sphere is coated with gold, nickel, cadmium, aluminum, silver, alumina, aluminum oxide, titanium oxide, or a combination thereof.

7. The method of claim 1, wherein one of the spectrums of light emulates natural light.

8. The method of claim 1, further comprising selectively controlling the individual light elements so that the oral cavity can be viewed under visible light that includes blue wavelengths.

9. The method of claim 8, wherein the visible light emulates incandescent light.

10. The method of claim 8, wherein the visible light emulates fluorescent light.

* * * * *